United States Patent
Yoo et al.

(10) Patent No.: US 10,251,919 B2
(45) Date of Patent: Apr. 9, 2019

(54) **METHOD FOR IMPROVING SKIN CONDITION OR ANTI-MICROORGANISMS OR ANTI-OXIDATION USING *LACTOBACILLUS SAKEI* MD HONEYSUCKLE**

(71) Applicant: AMOREPACIFIC CORPORATION, Seoul (KR)

(72) Inventors: Se Jin Yoo, Yongin-si (KR); Myeong Jin Goh, Yongin-si (KR); Sung Hoon Lee, Yongin-si (KR); Yong Jin Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 171 days.

(21) Appl. No.: 15/018,779

(22) Filed: Feb. 8, 2016

(65) Prior Publication Data

US 2016/0228477 A1    Aug. 11, 2016

(30) Foreign Application Priority Data

Feb. 9, 2015    (KR) .................... 10-2015-0019321

(51) Int. Cl.
| | | |
|---|---|---|
| *A61K 35/747* | (2015.01) | |
| *A61K 36/35* | (2006.01) | |
| *A61Q 19/08* | (2006.01) | |
| *A61Q 19/02* | (2006.01) | |
| *A61Q 17/00* | (2006.01) | |
| *A61K 8/98* | (2006.01) | |

(52) U.S. Cl.
CPC ............ *A61K 35/747* (2013.01); *A61K 8/988* (2013.01); *A61K 36/35* (2013.01); *A61Q 17/005* (2013.01); *A61Q 19/02* (2013.01); *A61Q 19/08* (2013.01); *A61K 2800/522* (2013.01); *Y02A 50/471* (2018.01); *Y02A 50/473* (2018.01); *Y02A 50/481* (2018.01)

(58) Field of Classification Search
CPC ............ A61K 2800/522; A61K 35/747; A61K 36/35; A61Q 19/08
IPC .............................. A61K 35/747; A61Q 19/08
See application file for complete search history.

(56) References Cited

PUBLICATIONS

Shuwen Zhang, et al., "Antioxidative activity of lactic acid bacteria in yogurt", African Journal of Microbiology Research, Dec. 9, 2011, vol. 5, No. 29, pp. 5194-5201.
Sung Hee Chung, et al., "Isolation of Flavonoids from Carthami Flos and their Antioxidative Activity", Yakhak Hoeji, vol. 52, No. 4, pp. 241-251, (2008).

*Primary Examiner* — Padmavathi Baskar
(74) *Attorney, Agent, or Firm* — Cantor Colburn LLP

(57) ABSTRACT

The present disclosure discloses a method for improving the skin condition or anti-microorganisms or anti-oxidation using *Lactobacillus sakei* MD_honeysuckle (accession number: KCTC 12675BP) derived from *Lonicera japonica* Thunb. A composition containing the strain or a cultured product thereof, or an extract thereof as an active ingredient has superior DPPH radical scavenging activity and antimicrobial activity against pathogenic microorganisms, has a high total polyphenol content and is capable of inhibiting the growth of melanocytes. Accordingly, the composition of the present disclosure is effective in preventing aging, improving skin wrinkles, whitening skin, fighting against microorganisms and fighting against oxidation and can be widely used in cosmetic compositions, pharmaceutical compositions or health food compositions where such effects are required.

8 Claims, 13 Drawing Sheets

Specification includes a Sequence Listing.

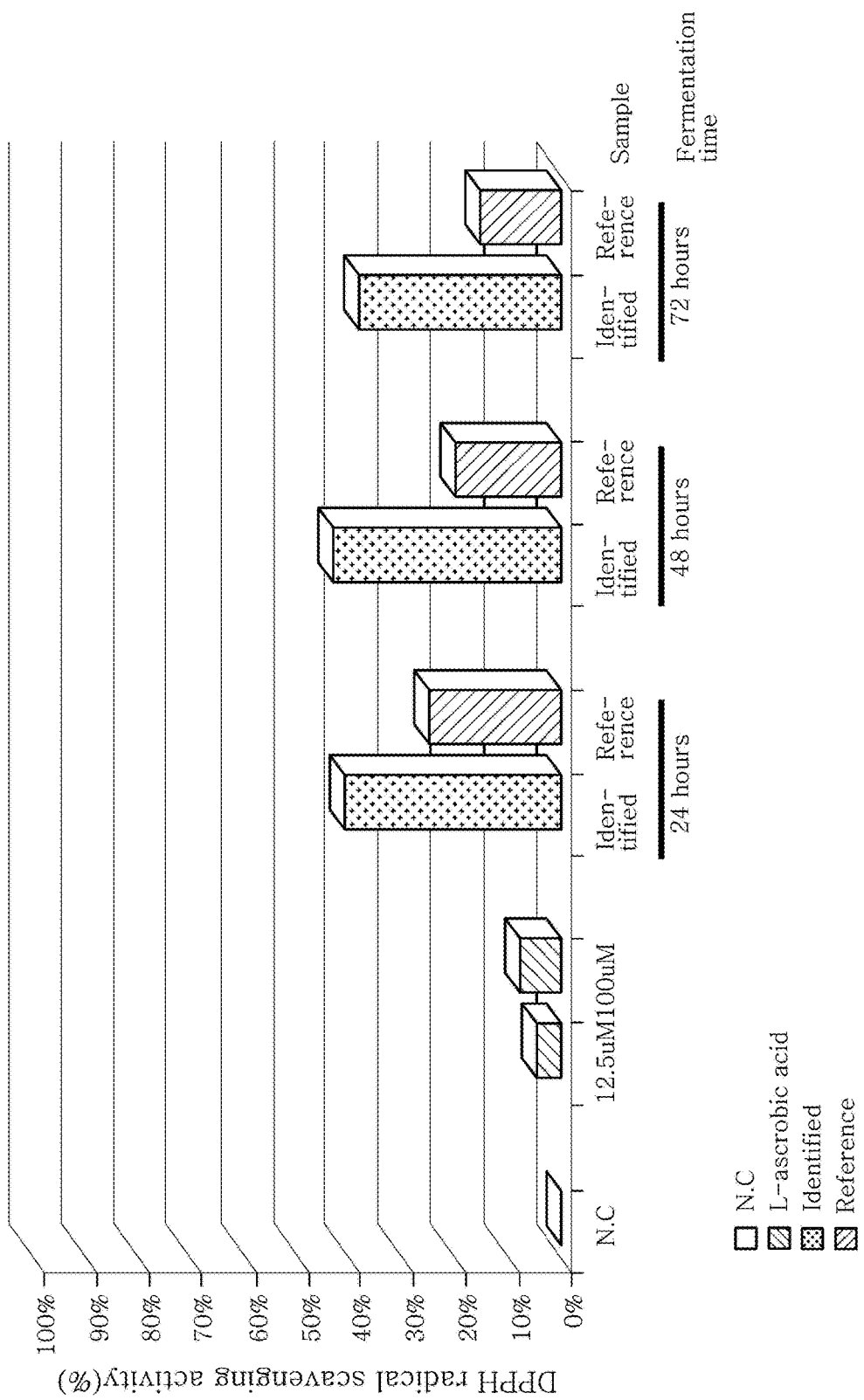

Fig.10

TTTTTGATTTTTTATCTCGACCCAGGCGAACGCTGACCGCGTGCTAATACATCCAAGTCGAACGCACTCT
GTTAGATTGAAGGAGCTTGCTCCTGATTGATAAACATTTGAGTGGCGGACGGGTGACTAACACGTGGG
TAACCTGCCCTAAGTGGGGGATAACAGATGCTAATACCGCATAAACCTAACACCGATGGT
GTAGGGTTGAAAGATGGTTTCGGCTATCACTTTAGGATGGACCGCGGTGCATTAGTTAGTTGGTGAGGTAAA
GGCTCACCAAGACCGTGATGCAGTAGGAGCAGTAGGAATCTTCCACAATGACGCACAGACGGCCCA
AGACTCTACGGGAGGCAGCAGTAGGGAATCTTCCACAATGACGCACAGTCTGATGGAGCAACGCCGGTG
AGTGAAGAAGGTTTTCGGATCGTAAAACTCTGTTGTTGAGAAGAAGATGTATCGATAGTAACTGATCAGGTAGT
GACGGTATCCAACCAGAAGCACCGGCTAACTACGTGCCAGCAGCCGCGGTAATACGTAGGTGGCAAGCGTT
GTCCGGAATTATTGGGCGTAAAGCGAGCGCAGGCGGTTTCTTAAGTCTGATGTGAAAGCCTTCGGCTCAACCG
AAGAAGTGCATCGAAACTGGGAAACTGAGTGCAGAAGAGGACAGTGGAACTCCATGTGTAGCGGTGAAA
TGCGTAGATATATGGAAGAACACCAGTGGCGAAGGCGGCTGTCTGGTCTGTAAACTGACGCTGAGGCTCGAAA
GCATGGGTAGCAAACAGGATTAGATACCCTGGTAGTCCATGCCGTAAACGATGAGTGCTAGGTGTTGGAGGGT
TTCCGCCCTTAGTGCCGCAGCTAACGCATTAAGCACTCCGCCTGGGGAGTACGACCGCAAGGTTGAAACTC
AAAGGAATTGACGGGGCCCCGCACAAGCGGTGGAGCATGTGGTTTAATTCGAAGCAACGCGAAGAACCTTA
CCAGGTCTTGACATCCTTTGACCACTCTAGAGATAGAGCTTTCCCTTCGGGACAAAGTGACAGGTGGTGCAT
GGTTGTCGTCAGCTCGTGTCGTGAGATGTTGGGTTAAGTCCCGCAACGAGCGCAACCCTTATTACTAGTTGCCA
GCATTTAGTTGGGCACTCTAGTGAGACTGCCGGTGACAAACCGGAGGAAGGTGGGGACGACGTCAAATCATC
ATGCCCCTTATGACCTGGGCTACACACGTGCTACAATGGATGTACAAAGAGTTGCGAGACCGCGAGGTTAG
CTAATCTCTAAAACCATTCTCAGTTCGGATTGTAGGCTGCAACTCGCCTACATGAAGCCGGAATCGCTAGTAAT
CGCGGATCAGCATGCCGCGGTGAATACGTTCCCGGGCCTTGTACACACCGCCCGTCACACCATGAGAGTTTGT
AACACCCAAAGCCGGTGAGGTACCCTGGGGAGCCGCGTCTGTGTCTGTTAA

SEQUENCE LISTING

<160> NUMBER OF SEQ ID NOS: 3

<210> SEQ ID NO 1
<211> LENGTH: 1506
<212> TYPE: DNA
<213> ORGANISM: Lactobacillus sakei MD_honeysuckle
<220> FEATURE:
<223> OTHER INFORMATION: 16s rRNA gene

<400> SEQUENCE: 1

```
tttttttgatt tttttatctc gacccaggcg aacgctgacc gcgtgcctaa tacatccaag      60
tcgaacgcac tctcgtttag attgaaggag cttgctcctg attgataaac atttgagtga     120
gtggcggacg ggtgactaac acgtgggtaa cctgccctaa agtgggggat aacatttgga     180
aacagatgct aataccgcat aaaacctaac accgcatggt gtagggttga agatggtttt    240
cggctatcac tttaggatgg acccgcggtg cattagttag ttggtgaggt aaaggctcac     300
caagaccgtg atgcatagcc gacctgagag ggtaatcggc cacactggga ctgagacacg     360
gcccagactc ctacgggagg cagcagtagg gaatcttcca caatggacga cagtctgatg     420
gagcaacgcc gcgtgagtga agaaggtttt cggatcgtaa aactctgttg tttgagaaga     480
atgtatctga tagtaactga tcaggtagtg acggtatcca accagaaagc cacggctaac     540
tacgtgccag cagccgcggt aatacgtagg tggcaagcgt tgtccggatt tattgggcgt     600
aaagcgagcg caggcggttt cttaagtctg atgtgaaagc cttcggctca accgaagaag     660
tgcatcgaaa cctgggaaac ttgagtgcag aagaggacag tggaactcca tgtgtagcgg     720
tgaaatgcgt agatatatgg aagaacacca gtggcgaagg cggctgtctg gtctgtaact     780
gacgctgagg ctcgaaagca tgggtagcaa acaggattag ataccctggt agtccatgcc     840
gtaaacgatg agtgctaggt gttggagggt ttccgcccct tagtgccgca gctaacgcat     900
taagcactcc gcctggggag tacgaccgca aggttgaaac tcaaaggaat tgacggggggc    960 ccgcacaagc ggtggagcat gtggtttaat tcgaagcaac gcgaagaacc ttaccaggtc   1020
ttgacatcct ttgaccactc tagagataga gctttccctt cggggacaaa gtgacaggtg   1080
gtgcatggtt gtcgtcagct cgtgtcgtga gatgttgggt taagtcccgc aacgagcgca   1140
acccttatta ctagctgcca gcatttagtt gggcactcta gtgagactgc cggtgacaaa   1200
ccggaggaag gtggggacga cgtcaaatca tcatgcccct tatgacctgg gctacacacg   1260
tgctacaatg gatggtacaa cgagttgcga gaccgcgagg tttagctaat ctcttaaaac   1320
cattctcagt tcggattgta ggctgcaact cgcctacatg aaaccggaat cgctagtaat   1380
cgcggatcag catgccgcgg tgaatacgtt cccgggcctt gtacacaccg cccgtcacac   1440
```

-continued

```
catgagagtt tgtaacaccc aaagccggtg aggtaccctg gggagccgcg tcttgtgtct    1500
cgttaa                                                              1506

<210> SEQ ID NO 2
<211> LENGTH: 20
<212> TYPE: DNA
<213> ORGANISM: Artificial sequence
<220> FEATURE:
<223> OTHER INFORMATION: primer_27F

<400> SEQUENCE: 2
agagtttgat cmtggctcag                                               20

<210> SEQ ID NO 3
<211> LENGTH: 22
<212> TYPE: DNA
<213> ORGANISM: Artificial sequence
<220> FEATURE:
<223> OTHER INFORMATION: primer_1492R

<400> SEQUENCE: 3
tacggytacc ttgttacgac tt                                            22
```

METHOD FOR IMPROVING SKIN CONDITION OR ANTI-MICROORGANISMS OR ANTI-OXIDATION USING *LACTOBACILLUS SAKEI* MD HONEYSUCKLE

CROSS-REFERENCE TO RELATED APPLICATION

This application claims the priority of Korean Patent Application No. 10-2015-0019321, filed on Feb. 9, 2015, and all the benefits accruing therefrom under 35 U.S.C. § 119, the contents of which in its entirety are herein incorporated by reference.

BACKGROUND

1. Field

The present disclosure discloses a method for improving the skin condition or anti-microorganisms or anti-oxidation using *Lactobacillus sakei* MD_honeysuckle derived from *Lonicera japonica* Thunb.

2. Description of the Related Art

Lactic acid bacteria collectively refer to bacteria which produce lactic acid as a major metabolite. Since long before the advancement of modern science, humans have utilized the unique characteristics of lactic acid bacteria either knowingly or unknowingly. Lactic acid bacteria are one of the most beneficial bacteria for human. Throughout long history, they have been widely utilized in human lives including fermented dairy products, other fermented foods such as fermented pastes, kimchi and fermented sausages, probiotics and feed additives. Lactic acid bacteria are widely distributed in nature, including the digestive tract, mouth or vagina of human or mammals, various fermented foods and soil. The lactic acid bacteria are one of the beneficial symbionts for human which are closely related to human lives either directly or indirectly.

The lactic acid bacteria are facultative anaerobic or obligate anaerobic bacteria that proliferate well under conditions of limited oxygen. The lactic acid bacteria can be divided into five genera, which are *Streptococcus, Pediococcus, Leuconostoc, Bifidobacteria* and *Lactobacillus*. Among them, the bacteria in the genus *Lactobacillus* homofermentative or heterofermentative bacteria commonly found during the fermentation of dairy products or vegetables.

Recently, with the increased interests in the efficacy of lactic acid bacteria, researches are actively underway on the development of the bacteria in the genus *Lactobacillus* as probiotics, food additives, etc. Through continued studies on the bacteria in the genus *Lactobacillus*, the inventors of the present disclosure have completed the present disclosure by isolating the novel strain *Lactobacillus sakei* from *Lonicera japonica* Thunb.

REFERENCES OF THE RELATED ART

Non-Patent Documents (Non-patent document 1) Sung Hee Chung et al, Isolation of Flavonoid from Carthami Flos and their Antioxidative Activity (2008), *Yakhak Hoeji,* 52(4), pp. 241-251.
(Non-patent document 2) Stephane Chaillou et al, The complete genome sequence of the meat-borne lactic acid bacterium *Lactobacillus sakei* 23K (2005), *Nature Biotechnology,* 23(12), pp. 1527-1533.
(Non-patent document 3) Shuwen Zhang et al, Antioxidative activity of lactic acid bacteria in yogurt (2011), *African Journal of Microbiology Research,* 5(29), pp. 5194-5201.

SUMMARY

In an aspect, the present disclosure is directed to providing a composition containing *Lactobacillus sakei* MD_honeysuckle (accession number: KCTC 12675BP) or a cultured product thereof as an active ingredient.

In another aspect, the present disclosure is directed to providing a composition containing *Lactobacillus sakei* MD_honeysuckle (accession number: KCTC 12675BP) or a cultured product thereof as an active ingredient, which is useful as a cosmetic composition, a pharmaceutical composition or a health food composition.

In an aspect, the present disclosure provides a composition containing *Lactobacillus sakei* MD_honeysuckle (accession number: KCTC 12675BP), a lysate thereof, a cultured product thereof or an extract thereof as an active ingredient.

In an aspect, the present disclosure provides an anti-aging composition containing *Lactobacillus sakei* MD_honeysuckle (accession number: KCTC 12675BP), a lysate thereof, a cultured product thereof or an extract thereof as an active ingredient.

In another aspect, the present disclosure provides a composition for whitening skin, which contains *Lactobacillus sakei* MD_honeysuckle (accession number: KCTC 12675BP), a lysate thereof, a cultured product thereof or an extract thereof as an active ingredient.

In another aspect, the present disclosure provides a composition for improving skin wrinkles, which contains *Lactobacillus sakei* MD_honeysuckle (accession number: KCTC 12675BP), a lysate thereof, a cultured product thereof or an extract thereof as an active ingredient.

In another aspect, the present disclosure provides an antimicrobial composition containing *Lactobacillus sakei* MD_honeysuckle (accession number: KCTC 12675BP), a lysate thereof, a cultured product thereof or an extract thereof as an active ingredient.

In another aspect, the present disclosure provides an antioxidant composition containing *Lactobacillus sakei* MD_honeysuckle (accession number: KCTC 12675BP), a lysate thereof, a cultured product thereof or an extract thereof as an active ingredient.

In an aspect, the present disclosure provides a composition containing *Lactobacillus sakei* MD_honeysuckle (accession number: KCTC 12675BP) or a cultured product thereof as an active ingredient. The composition of the present disclosure has superior DPPH radical scavenging activity and antimicrobial activity against pathogenic microorganisms, has a high total polyphenol content and is capable of inhibiting the growth of melanocytes. Accordingly, the composition of the present disclosure is effective in preventing aging, improving skin wrinkles, whitening skin, fighting against microorganisms and fighting against oxidation and can be widely used in cosmetic compositions, pharmaceutical compositions or health food compositions where such effects are required.

BRIEF DESCRIPTION OF THE DRAWINGS

FIG. 6 shows the result of measuring the DPPH assay radical scavenging activity of the identified strain and the reference strain.

FIG. 10 shows the 16S rRNA gene sequence of *Lactobacillus sakei* MD_honeysuckle (SEQ ID NO 1).

DETAILED DESCRIPTION

Figure 1:
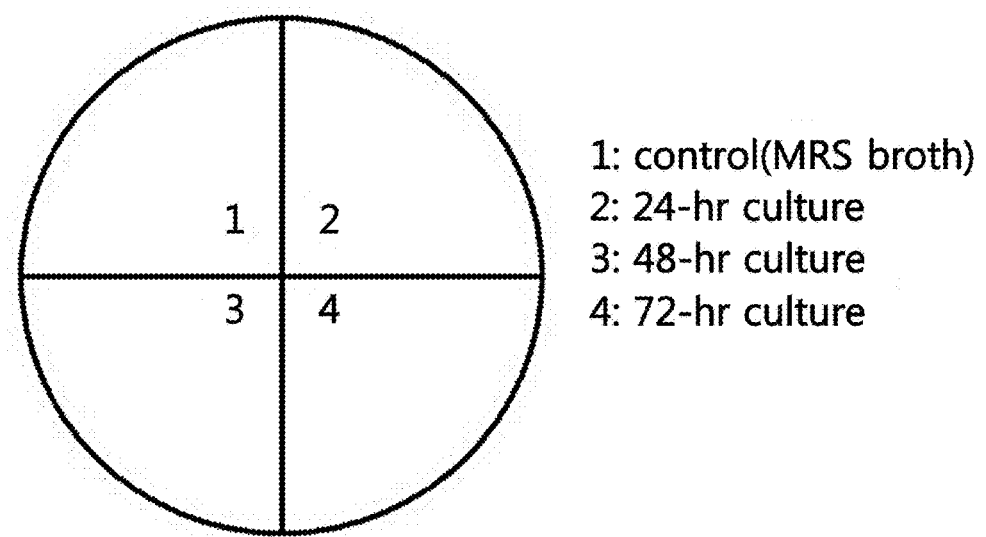
FIG. 1 shows the segments of a paper disk used in agar disk diffusion assay.

Hereinafter, the present disclosure is described in detail.

In an aspect, the present disclosure provides a method for improving the skin condition of a subject, which includes a step of administering an effective amount of a *Lactobacillus sakei* MD_honeysuckle (accession number: KCTC 12675BP) strain, a lysate thereof, a cultured product thereof or an extract thereof to a subject in need thereof.

In this aspect, the method for improving the skin condition may be for preventing or improving aging of the subject.

In this aspect, the method for improving the skin condition may be for whitening the skin of the subject. In this aspect, the method may be for inhibiting the production of melanocytes.

In this aspect, the method for improving the skin condition may be for preventing or improving skin wrinkles of the subject.

In another aspect, the present disclosure provides a method for anti-microorganisms in a subject, which includes a step of administering an effective amount of a *Lactobacillus sakei* MD_honeysuckle (accession number: KCTC 12675BP) strain, a lysate thereof, a cultured product thereof or an extract thereof to a subject in need thereof. In this aspect, the microorganisms may belong to one or more of the genera *Escherichia*, *Staphylococcus*, *Salmonella* and *Vibrio*. Specifically, the microorganism may be *Escherichia coli* K12W3110, *Staphylococcus aureus* (ATCC 65389), *Salmonella typhiurium* (accession number: KCTC 2053) or *Vibrio cholerae* (KCTC 2730), although not being limited thereto.

In another aspect, the present disclosure provides a method for anti-oxidation in a subject, which includes a step of administering an effective amount of a *Lactobacillus sakei* MD_honeysuckle (accession number: KCTC 12675BP) strain, a lysate thereof, a cultured product thereof or an extract thereof to a subject in need thereof. In this aspect, the *Lactobacillus sakei* MD_honeysuckle (accession number: KCTC 12675BP), the lysate thereof, the cultured product thereof or the extract thereof may exhibit 5 times or higher DPPH radical scavenging activity, which is calculated as the difference in the absorbance of a sample at 515 nm before and after reaction with DPPH (diphenylpicrylhydrazyl) divided by the absorbance of the sample at 515 nm before the reaction with the DPPH, when the *Lactobacillus sakei* MD_honeysuckle (accession number: KCTC 12675BP), the lysate thereof, the cultured product thereof or the extract thereof is used as the sample as compared to when L-ascorbic acid is used as the sample, although not being limited thereto. For example, it may exhibit 2 times or higher, 3 times or higher, 4 times or higher, 5 times or higher, 6 times or higher, 7 times or higher, 8 times or higher, 9 times or higher, 10 times or higher or 11 times or higher DPPH radical scavenging activity.

In the present disclosure, a fermented product may refer to a substance produced during fermentation of *Lactobacillus sakei*. For example, it may refer to a metabolite contained in a fermented broth.

In the present disclosure, the *Lactobacillus sakei* MD_honeysuckle (accession number: KCTC 12675BP) may be derived from *Lonicera japonica* Thunb.

In the present disclosure, the *Lonicera japonica* Thunb. may refer to a semievergreen vine-like shrub belonging to the family Caprifoliaceae. It is also called honeysuckle. The variety var. repens has brown hair on young twigs and leaves, whereas the variety var. chinensis has little hair except the leaf edges and has reddish flowers whose upper petals are divided more than half. The *Lonicera japonica* Thunb. grow in the woods, hills and towns throughout Korea. The vine twines clockwise and reaches up to 3 m. The reddish-brown young twig is hairy and hollow. The leaves are lanceolate or oval, opposite and dull at the end. The leave are 3-8 cm long and 1-3 cm broad and have smooth edges. One or two flowers bloom in June or July on the axillae. The petals, which are 3-4 cm long, open white and fade soon to yellow. The end of the petal is divided into five parts and one of them is bent backwards. There are curved hairs inside the petal together with five stamens and one pistil. The fruit, which ripens in September to October, is 7-8 mm in diameter. The main ingredients are luteolin, inositol and tannin.

In the present disclosure, the *Lactobacillus sakei* MD_honeysuckle (accession number: KCTC 12675BP) may contain a 16S rRNA gene sequence of SEQ ID NO 1.

In the present disclosure, the *Lactobacillus sakei* MD_honeysuckle (accession number: KCTC 12675BP), the lysate thereof, the cultured product thereof or the extract thereof may be administered in the form of a composition and the composition may be a cosmetic, pharmaceutical or health food composition.

Specifically, the cosmetic composition may be, for example, a hair cosmetic, a body cosmetic, a base cosmetic, a makeup cosmetic, etc. Its formulation is not particularly limited and may be selected adequately depending on purposes.

For example, the cosmetic composition may be formulated into a solution, a suspension, an emulsion, a paste, a gel, a cream, a lotion, a powder, a soap, a surfactant-containing cleanser, an oil, a powder foundation, an emulsion foundation, a wax foundation, a spray, etc., although not being limited thereto. More specifically, it may be formulated into a cleanser such as a shampoo, a rinse, a body cleanser, etc., a hair fixative such as hair tonic, a gel, a mousse, etc., a hair cosmetic such as a hair growth promoter, a hair dye, etc. or a base cosmetic such as a softening lotion, a nourishing lotion, a body lotion, a nourishing cream, a massage cream, a moisturizing cream, a hand cream, an essence, an eye cream, a cleansing cream, a cleansing foam, a cleansing water, a pack, a gel, a patch, an oil-in-water (O/W) emulsion, a water-in-oil (W/O) emulsion, etc.

The cosmetic composition may contain a cosmetically acceptable medium or matrix. It may be provided in the form of any formulation suitable for topical application, for example, a solution, a gel, a solid, an anhydrous paste, an oil-in-water emulsion, suspension, a microemulsion, a microcapsule, a microgranule, an ionic (liposomal) and/or non-ionic vesicular dispersion, a cream, a lotion, a powder, an ointment, a spray or a concealer stick. These compositions may be prepared by a method commonly employed in the art.

When the formulation of the present disclosure is a solution or an emulsion, a solvent, a solubilizer or an emulsifier may be used as a carrier component. For example, water, ethanol, isopropanol, ethyl carbonate, ethyl acetate, benzyl alcohol, benzyl benzoate, propylene glycol, 1,3-butylene glycol, an aliphatic ester of glycerol, polyethylene glycol or a fatty acid ester of sorbitan may be used.

When the formulation of the present disclosure is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier component.

When the formulation of the present disclosure is a paste, a cream or a gel, an animal oil, a vegetable oil, a wax, paraffin, starch, tragacanth, a cellulose derivative, polyethylene glycol, silicone, bentonite, silica, talc, zinc oxide, etc. may be used as a carrier component.

When the formulation of the present disclosure is a powder or a spray, lactose, talc, silica, aluminum hydroxide, calcium silicate or polyamide powder may be used as a carrier component. In particular, a spray may further contain a propellant such as chlorofluorohydrocarbon, propane/butane or dimethyl ether.

In an exemplary embodiment of the present disclosure, the cosmetic composition may further contain a thickener. The thickener contained in the cosmetic composition of the present disclosure may be methyl cellulose, carboxymethyl cellulose, carboxymethyl hydroxyguanine, hydroxymethyl cellulose, hydroxyethyl cellulose, carboxyvinyl polymer, polyquaternium, cetearyl alcohol, stearic acid, carrageenan, etc. Specifically, one or more selected from carboxymethyl cellulose, carboxyvinyl polymer, polyquaternium may be used. Most specifically, carboxyvinyl polymer may be used.

In an exemplary embodiment of the present disclosure, the cosmetic composition may contain various matrices and additives as desired and their kind and amount can be easily determined by those skilled in the art. The cosmetic composition may contain acceptable additives such as a preservative, a colorant, etc. commonly used in the art.

Specifically, the preservative may be phenoxyethanol, 1,2-hexanediol, etc. and a synthetic fragrance may be used.

Further, in an exemplary embodiment of the present disclosure, the cosmetic composition may contain a substance selected from a group consisting of a water-soluble vitamin, an oil-soluble vitamin, a polypeptide, a polysaccharide, a sphingolipid and a seaweed extract. In addition, it may further contain an oil, a fat, a humectant, an emollient, a surfactant, an organic or inorganic pigment, an organic powder, a UV absorbent, a preservative, a sterilizer, an antioxidant, a plant extract, a pH control agent, an alcohol, a colorant, a fragrance, a blood circulation stimulant, a cooling agent, an antiperspirant, purified water, etc.

However, the ingredients that may be contained in the cosmetic composition are not limited thereto and the amount of the ingredients may be determined within the range not negatively affecting the purpose and effect of the present disclosure.

A pharmaceutical composition according to an aspect of the present disclosure may be in the form of various oral or parenteral formulations. The formulation is prepared using a commonly used diluent or excipient such as a filler, an extender, a binder, a humectant, a disintegrant, a surfactant, etc. Solid formulations for oral administration include a tablet, a pill, a powder, a granule, a soft or hard capsule, etc. The solid formulation is prepared by mixing the active ingredient with at least one excipient, e.g., starch, calcium carbonate, sucrose, lactose, gelatin, etc. In addition to the simple excipient, a lubricant such as magnesium stearate, talc, etc. is also used. Liquid formulations for oral administration include a suspension, a liquid for internal use, an emulsion, a syrup, etc. In addition to a commonly used simple diluent such as water or liquid paraffin, various excipients, e.g., a humectant, a sweetener, an aromatic, a preservative, etc. may be contained. Formulations for parenteral administration include a sterilized aqueous solution, a non-aqueous solution, a suspension, an emulsion, a freeze-dried formulation and a suppository. For the non-aqueous solution or suspension, propylene glycol, polyethylene glycol, a vegetable oil such as olive oil, an injectable ester such as ethyl oleate, etc. may be used as a solvent. As a base of the suppository, witepsol, macrogol, tween 61, cocoa butter, laurin butter, glycerogelatin, etc. may be used.

In an aspect of the present disclosure, the pharmaceutical composition may also contain a pharmaceutically acceptable salt of the active ingredient and the active ingredient may be used either alone or in combination with another pharmaceutically active compound. The salt is not particularly limited as long as it is pharmaceutically acceptable. For example, hydrochloride, sulfate, nitrate, phosphate, hydrofluoride, hydrobromide, formate, acetate, tartrate, lactate, citrate, fumarate, maleate, succinate, methanesulfonate, benzenesulfonate, toluenesulfonate, naphthalenesulfonate, etc. may be used.

In an aspect of the present disclosure, the composition may be administered orally or parenterally depending on purposes. A daily administration dosage may be, for example, $10^5$-$10^{13}$ CFU/day, more specifically $10^6$-$10^{10}$ CFU/day, of *Lactobacillus sakei*, although not being limited thereto. The administration dosage for a particular patient may vary depending on the body weight, age, sex, physical condition and diet of the patient, administration time, administration method, rate of excretion, severity of a disease, etc.

The pharmaceutical composition according to an aspect of the present disclosure may be prepared into any suitable pharmaceutical formulation, including an oral formulation such as a powder, a granule, a tablet, a soft or hard capsule, a suspension, an emulsion, a syrup, an aerosol, etc., a formulation for external application to skin such as an ointment, a cream, etc., a suppository, an injection, a sterilized solution for injection, etc., according to a common method. Specifically, it may be prepared into an injection or a formulation for external application to skin.

The composition according to an aspect of the present disclosure may be administered to a mammal such as rat, mouse, cattle, human, etc. through various routes including parenteral and oral routes. All modes of administration may be expected. For example, it may be administered orally, transdermally, intravenously, intramuscularly or subcutaneously.

The composition according to an aspect of the present disclosure may be administered through various routes that can be easily adopted by those of ordinary skill in the art. In particular, the pharmaceutical composition according to an aspect of the present disclosure may be administered by being applied on skin as a formulation for external application to skin.

In an aspect of the present disclosure, the composition may be a food composition and the food composition may be a health functional food composition. For example, it may be a fermented food composition including tea, dairy products, kimchi and brewed beverages.

The food composition according to an aspect of the present disclosure may be formulated, for example, into a tablet, a granule, a powder, a liquid such as a drink, a caramel, a gel, a bar, etc. Each formulation of the food composition may contain, in addition to the active ingredient, ingredients commonly used in the art that can be easily selected by those skilled in the art considering the particular formulation or purpose of use. In this case, a synergic effect may occur.

In the food composition according to an aspect of the present disclosure, determination of the administration dosage of the active ingredient is within the level of those skilled in the art. A daily administration dosage may be, for example, $10^5$-$10^{13}$ CFU/day, more specifically $10^6$-$10^{10}$ CFU/day, of Lactobacillus sakei, although not being limited thereto. The administration dosage may vary depending on various factors such as the age and health condition of a subject, presence of complication(s), etc.

In an aspect of the present disclosure, the food composition may further contain various nutrients, vitamins, minerals (electrolytes), flavors such as synthetic flavors or natural flavors, colorants, extenders (cheese, chocolate, etc.), pectic acid and salts thereof, alginic acid and salts thereof, organic acids, protective colloidal thickeners, pH control agents, stabilizers, preservatives, glycerin, alcohols, carbonating agents used in carbonated beverage, etc. In addition, in an aspect of the present disclosure, a functional food composition may contain a pulp for preparing a natural fruit juice, a fruit juice drink or a vegetable drink. These ingredients may be used either independently or in combination. The mixing ration of these additives is of no significant importance. In an aspect of the present disclosure, the additives may be contained in an amount of about 0-20 parts by weight based on 100 parts by weight of the composition.

The Lactobacillus strain Lactobacillus sakei MD_honeysuckle was deposited on Sep. 11, 2014 in the Korean Collection for Type Cultures (KCTC) and was given the accession number KCTC 12675BP.

Hereinafter, a method for isolating and identifying novel Lactobacillus sakei MD_honeysuckle according to the present disclosure and characteristics thereof will be described in detail through examples and test examples. However, the following examples and test examples are for illustrative purposes only and the category and scope of the present disclosure are not limited by them.

[Example 1] Isolation and Identification of Lactobacillus sakei MD_Honeysuckle

The flower of Lonicera japonica Thunb. was serially diluted with distilled water and applied on a MRS (de Man, Rogosa and Sharpe) agar plate. After culturing at 30° C., black colonies were taken. The procedure was repeated until a single strain colony was obtained.

The single strain was identified as Lactobacillus sakei MD_honeysuckle by comparing similarity with Lactobacillus sakei (KCTC 13416, hereinafter referred to as a reference strain) through 16S rRNA sequencing as described below.

[Example 1-1] Culturing of Strain

The single colony obtained in Example 1 was inoculated to 100 mL of a MRS (de Man, Rogosa and Sharpe) broth (Difco) and a culture of Lactobacillus sakei MD_honeysuckle was obtained by cultuirng at 30° C.

[Example 1-2] Extraction of DNA

DNA was extracted using the FastDNA spin for soil kit (MP Biomedicals, France) according to the manufacturer's protocol. Specifically, after adding 978 μL of the sample and 122 μL of MT buffer to a lysing matrix E tube, followed by vortexing for 5 minutes, centrifugation was performed at 14,000 rpm for 10 minutes. After the centrifugation, the supernatant was transferred to a 2-mL catch tube. After adding 250 μL of PPS and inverting 10 times, centrifugation was performed again at 14,000 rpm and the supernatant was transferred to a fresh 2-mL catch tube. After adding 1 mL of a binding matrix solution and allowing to precipitate at room temperature for 3 minutes, 500 μL of the supernatant was removed and the remaining solution was resuspended and then 600 μL was taken and added to a spin filter. After centrifuging at 14,000 rpm for 1 minute, the binding matrix in the filter was resuspended using SEWS-M. After centrifuging again at 14,000 rpm for 1 minute, followed by washing 2 times, the filter was completely dried at room temperature. Then, the strain DNA was obtained by adding 50 μL of a DES solution and centrifuging at 14,000 rpm for 1 minute.

[Example 1-3] PCR (Amplification of 16S rRNA Gene)

16S rRNA gene was amplified using the strain-specific primer 27F and the universal primer 1492R (Table 1). The reaction solution consisted of 2 μL of 10× PCR buffer, 1 μL of 25 mM MgCl$_2$, 2 μL of 10 mM dNTPs, 1 μL of a forward primer (10 pmol), 1 μL of a reverse primer (10 pmol) and 0.5 μL of 0.5 unit Taq polymerase, and the total volume of the reaction solution was 20 μL. PCR reaction was conducted by 30 cycles of 1 minute at 95° C., 1 minute at 55° C. and 1 minute and 30 seconds at 75° C. Finally, after treating at 72° C. for 8 minutes, the reaction solution was kept at 4° C.

The GeneAmp PCR system 9700 (Applied Biosystems, USA) was used as a PCR thermocycler. The amplified PCR product was electrophoresed on 1% agarose gel and specific bands were visualized by staining with ethidium bromide.

TABLE 1

| Primers | Sequence | Target DNAs |
|---|---|---|
| 27F (SEQ ID NO 2) | 5'-AGA GTT TGA TCM TGG CTC AG-3' | Bacterial 16S rDNA |
| 1492R (SEQ ID NO 3) | 5'-TAC GGY TAC CTT GTT ACG ACT T-3' | Universal 16S rDNA |

[Example 1-4] Analysis of Similarity to
Lactobacillus sakei (KCTC 13416)

Sequence analysis was conducted using the MEGA 4.1 (Center of Evolutionary Functional Genomics Biodesign Institute, USA) program. The phylogenic relationship of the 16S rRNA gene sequences of *Lactobacillus sakei* MD_Honeycuckle and *Lactobacillus sakei* (KCTC 13416) was analyzed. The similarity between the *Lactobacillus sakei* MD Honeycuckle and the *Lactobacillus sakei* (KCTC 13416) was about 63%.

[Example 2] Preparation of Cell-Free Filtrate 1 mL of the *Lactobacillus sakei* MD_honeysuckle obtained in Example 1 was inoculated to 100 mL of MRS broth. Then, while culturing for 3 days in a shaking incubator under the condition of 180 rpm and 37° C., 10-mL cultures were sampled with 24-hour intervals (at 24, 48 and 72 hours). The sampled cultures were centrifuged (3000 rpm, 15 minutes) and cell-free filtrates were obtained by filtering with a filter (pore size: 0.2 μm).

[Test Example 1] Agar Disk Diffusion Assay

[Test Example 1-1] Preparation of Cell-Free Filtrate

The cell-free filtrates of *Lactobacillus sakei* MD_honeysuckle obtained in Example 2 were prepared.

[Test Example 1-2] Culturing of Pathogenic Microorganisms

100 μL of each pathogenic microorganism (*Escherichia coli* K12W3110, *Staphylococcus aureus* (ATCC 65389), *Salmonella typhiurium* (KCTC 2053), *Vibrio cholerae* (KCTC 2730)) was inoculated to 10 mL of broth. After culturing for 24 hours in a shaking incubator under the condition of 180 rpm and 37° C., $OD_{600}$ was measured and the culture was diluted to about $10^6$ CFU/mL.

[Test Example 1-3] Application to Paper Disk

An 8-mm paper disk was soaked with 50 μL of the prepared cell-free filtrate. Then, the paper disk was dried for about 10-15 minutes.

Figure 2:
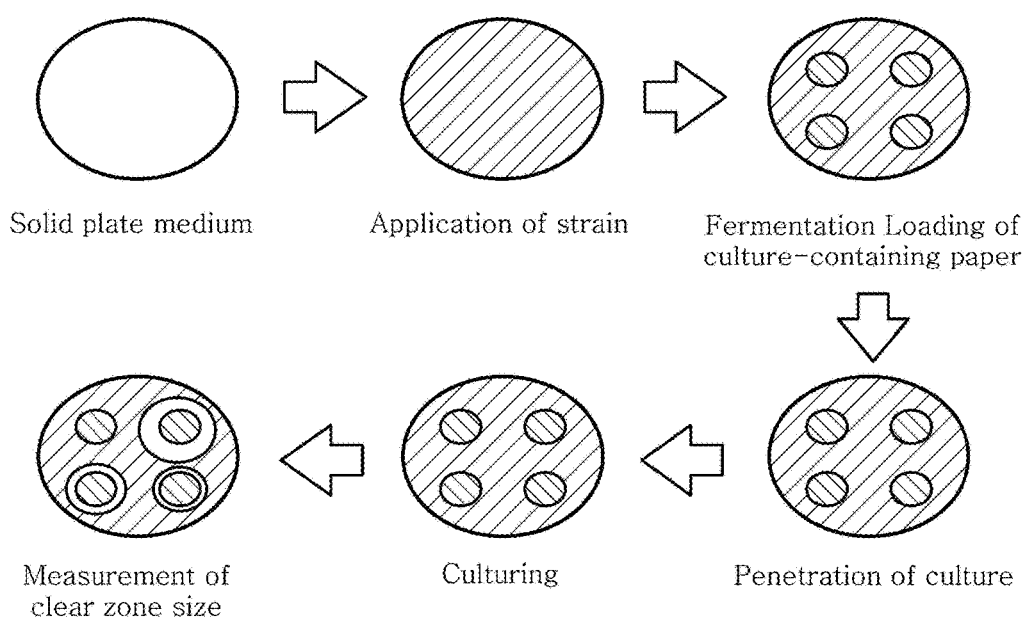
FIG. 2 describes the procedure of agar disk diffusion assay.

After applying 200 μL of the culture of the pathogenic microorganism obtained in Test Example 1-2 on an agar plate, paper disks were deposited on different segments using sterilized tweezers. In segment 1, a paper disk to which MRS broth was applied was deposited as a control. In segment 2, a paper disk to which the cell-free filtrate that had been cultured for 24 hours was applied was deposited. In segment 3, a paper disk to which the cell-free filtrate that had been cultured for 48 hours was applied was deposited. In segment 4, a paper disk to which the cell-free filtrate that had been cultured for 72 hours was applied was deposited (see FIG. 1 and FIG. 2).

After incubation in an incubator at 37° C. for 12 hours, formation of a clear zone was investigated.

The same experiment was conducted using *Lactobacillus sakei* (KCTC 13416) as a positive control.

Figure 3:
FIG. 3 shows the result of agar disk diffusion assay of *Lactobacillus sakei* MD_honeysuckle (accession number: KCTC 12675BP) for pathogenic microorganisms (*V. choleeerae*).
Figure 4:
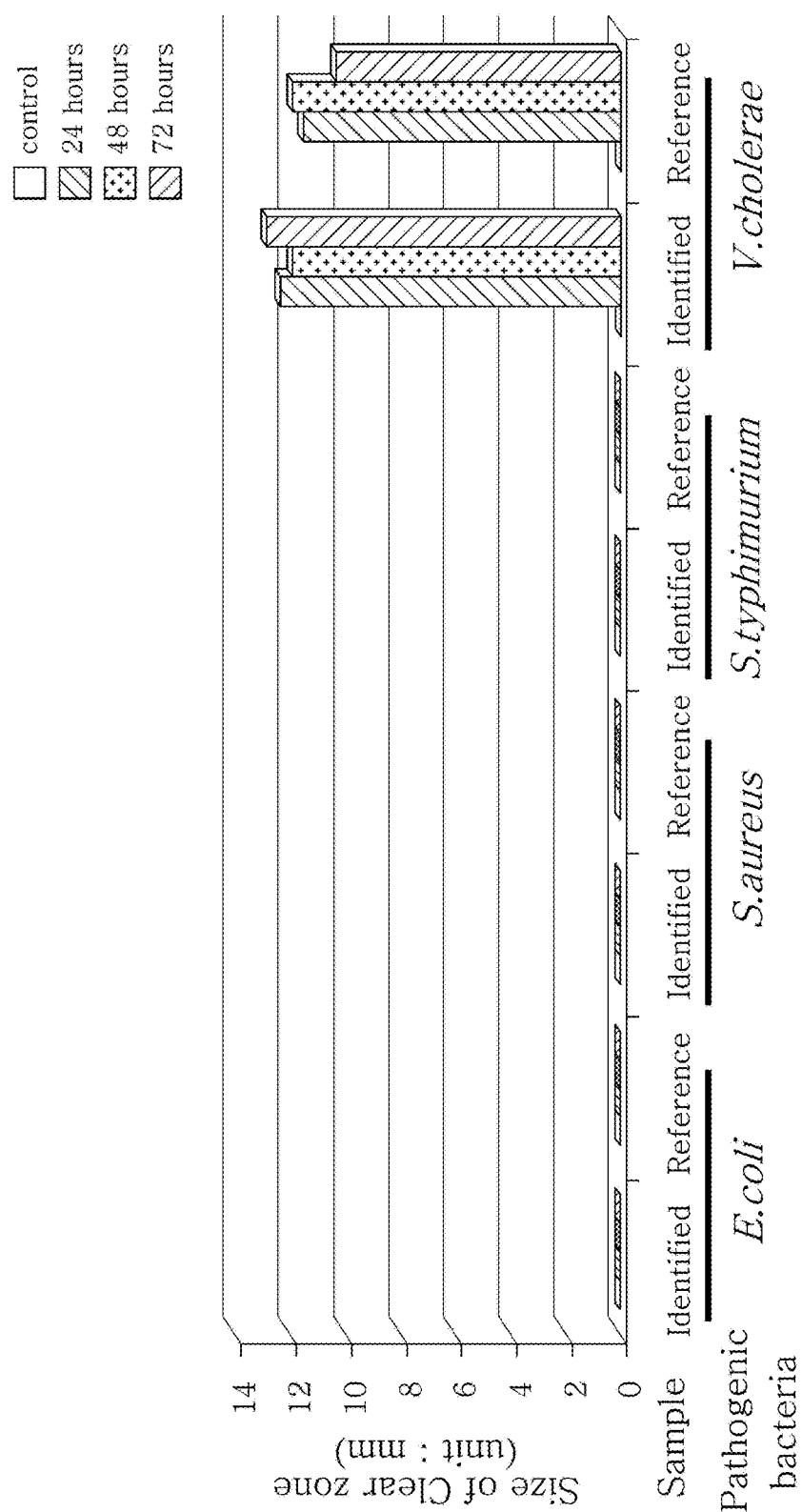
FIG. 4 shows the result of agar disk diffusion assay of the identified strain *Lactobacillus sakei* MD_honeysuckle (accession number: KCTC 12675BP) and the reference strain *Lactobacillus sakei* (accession number: KCTC 13416)) for 4 pathogenic microorganisms.
Figure 5A:
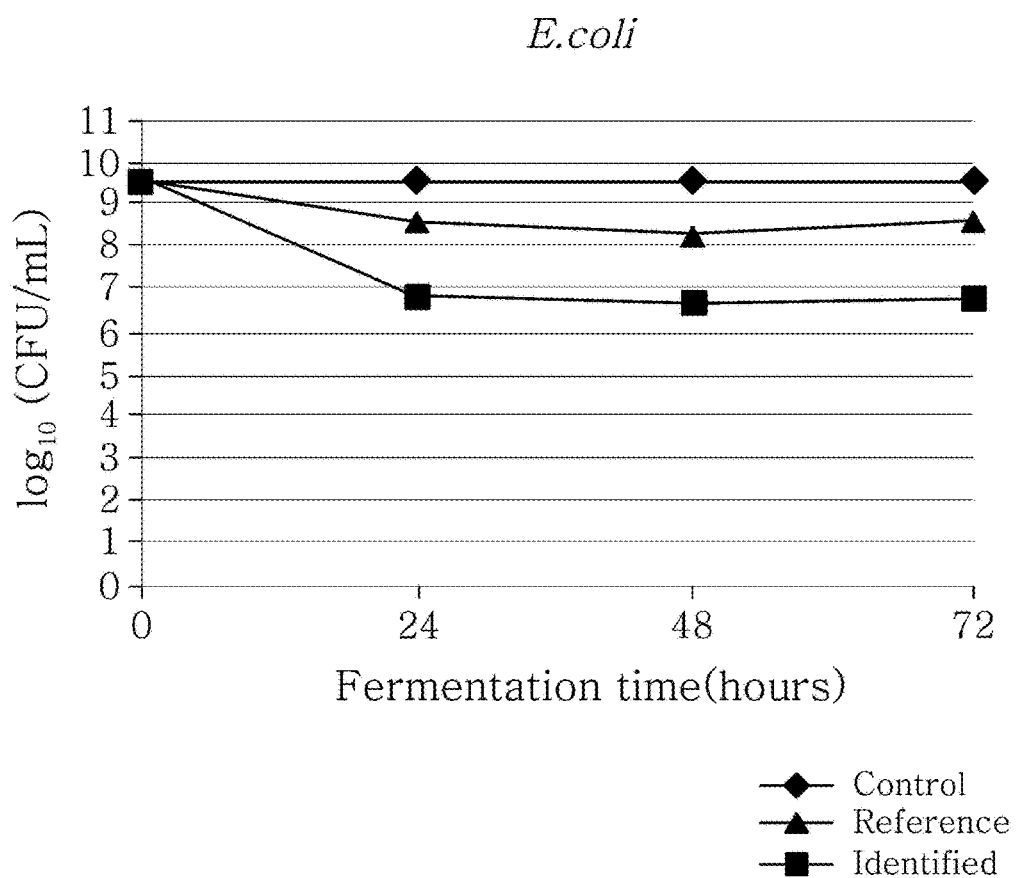
FIG. 5A to 5D show the result of colony counting of the identified strain and the reference strain (log(CFU/mL)).
Figure 5B:
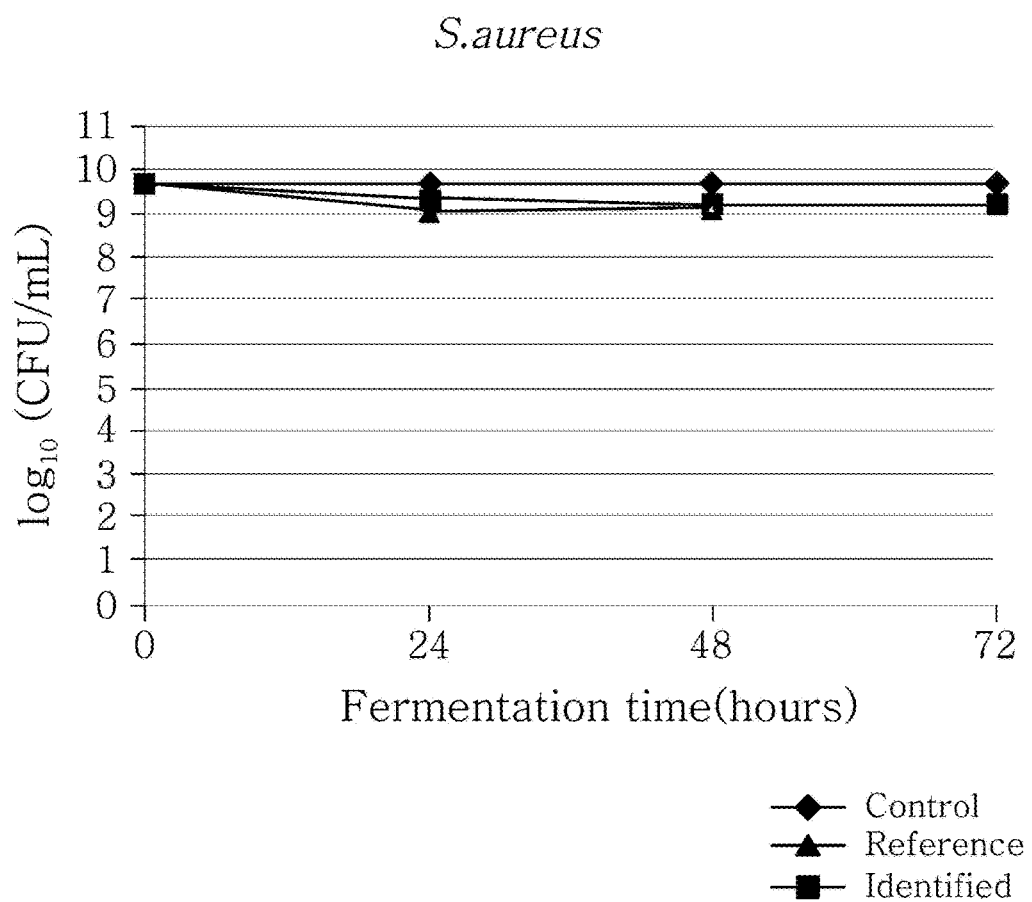
Figure 5C:
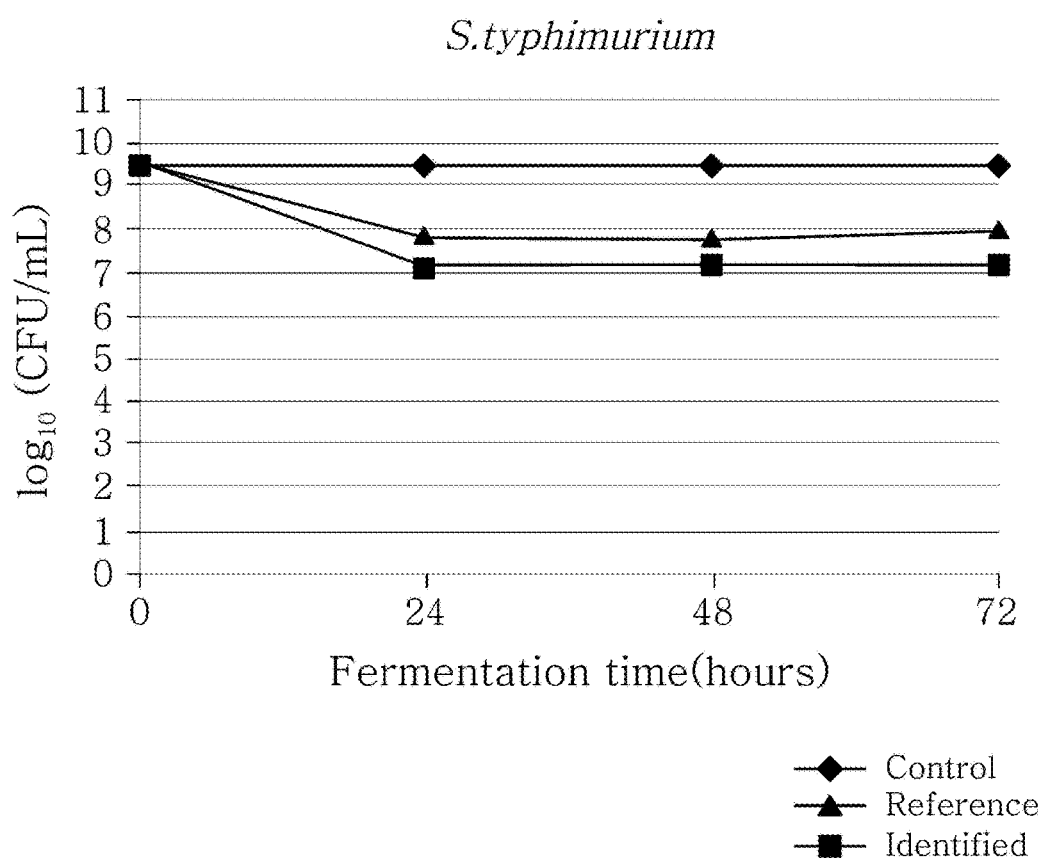
Figure 5D:
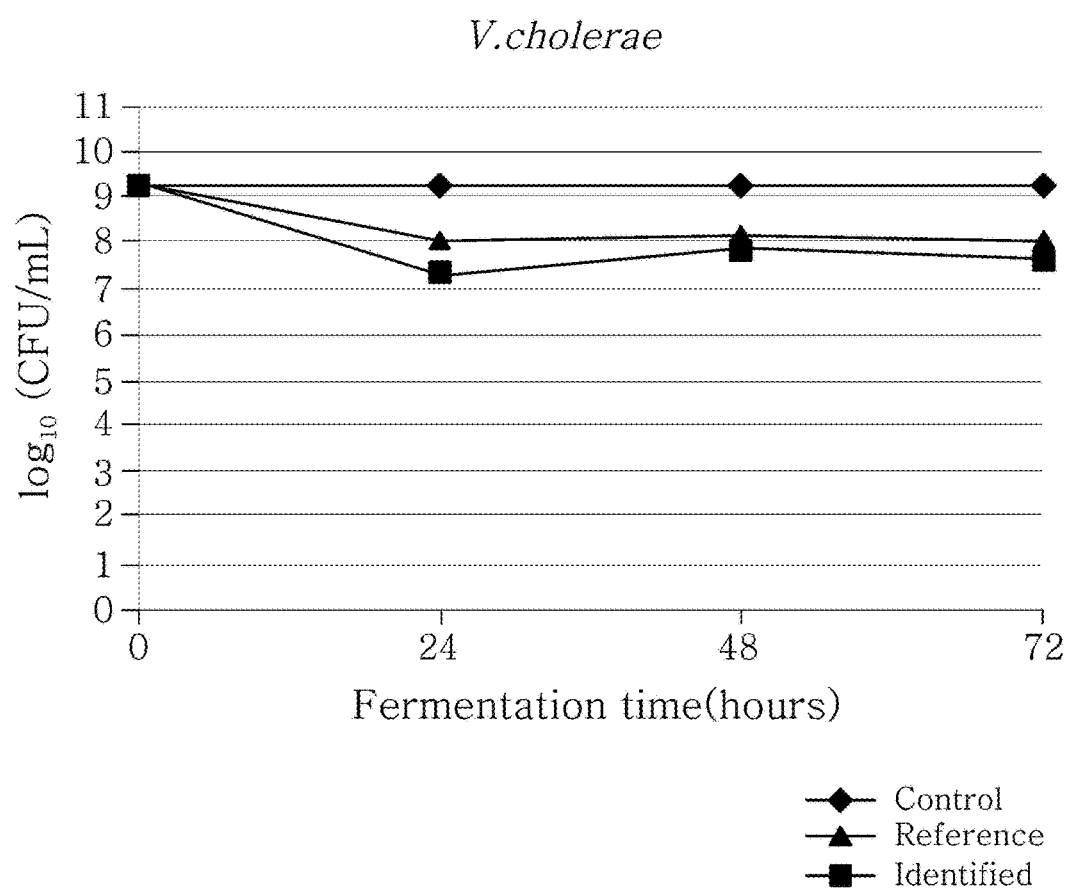

As can be seen from FIG. 3, a clear zone was observed on the plate on which *Vibrio cholerae* (KCTC 2730) was applied. It was also observed that a wider clear zone was formed for the strain of the present invention, *Lactobacillus sakei* MD_honeysuckle, than the *Lactobacillus sakei* (KCTC 13416) used as a positive control (see FIG. 4 and Table 2).

TABLE 2

| V. cholera | Clear zone diameter (mm) for identified strain | Clear zone diameter (mm) for reference strain |
| --- | --- | --- |
| Control (MRS broth) | 0 | 0 |
| 24-hr culture | 12 | 11 |
| 48-hr culture | 11.5 | 11.5 |
| 72-hr culture | 12.5 | 10 |

[Test Example 2] Colony Counting

[Test Example 2-1] Preparation of Cell-Free Filtrate

The cell-free filtrates of *Lactobacillus sakei* MD_honeysuckle obtained in Example 2 were prepared.

[Test Example 2-2] Culturing of Pathogenic Microorganisms

100 μL of each pathogenic microorganism (*Escherichia coli* K12W3110, *Staphylococcus aureus* (ATCC 65389), *Salmonella typhiurium* (KCTC 2053), *Vibrio cholerae* (KCTC 2730)) was inoculated to 10 mL of broth. The microorganism was cultured in a shaking incubator under the condition of 180 rpm and 37° C. to the mid-log phase ($OD_{500}$=0.4±0.1). Then, 100 μL of the culture was inoculated to a broth and then 400 μL of the cell-free filtrate was added to the broth. After culturing in a shaking incubator for 8 hours and diluting with a broth, 100 μL of the diluted culture was applied onto an agar plate. Subsequently, colony counting was conducted after culturing at 37° C. for 24 hours. After applying the serially diluted culture onto the solid medium, the number of colonies was counted on a plate where 100-200 colonies were formed and then the total number of microorganisms was calculated by multiplying by the dilution factor.

The same experiment was conducted also for the reference strain.

The logarithm of the obtained colony-forming unit (log (CFU/mL)) was calculated. A smaller logarithmic value means higher antimicrobial activity of the sample. The result is shown in FIG. 5.

[Test Example 3] DPPH Assay

20 μL of each of the cell-free filtrates (24 hr, 48 hr, 72 hr) obtained in Example 2 was reacted with 1 mL of 0.2 mM DPPH (Sigma Aldrich) for 30 minutes. L-Ascorbic acid (Sigma Aldrich) was used as a positive control. The L-ascorbic acid of the same volume as the cell-free filtrate of *Lactobacillus sakei* MD_honeysuckle was used at concentrations of 12.5 μM, 25 μM, 50 μM and 100 μM. MRS broth not treated with a strain was used as a negative control.

After the reaction, $OD_{515}$ was measured using a spectrophotometer and DPPH radical scavenging activity was calculated according to the following equation.

DPPH radical scavenging activity (%)=[(Absorbance of control to which sample was not added)−(Absorbance of group to which sample was added)]/(Absorbance of control to which sample was not added)

The same experiment was conducted also for the reference strain. The experiment was conducted 3 times and the average value was obtained. As seen from FIG. 6, the *Lactobacillus sakei* MD_honeysuckle exhibited better DPPH radical scavenging activity than the L-ascorbic acid as a positive control (the *Lactobacillus sakei* MD_honeysuckle exhibited average radical scavenging activity of 41%, whereas the L-ascorbic acid exhibited about 7% of radical scavenging activity at 100 μM) and the reference strain *Lactobacillus sakei* (KCTC 13416).

[Test Example 4] Measurement of Total Polyphenol Content

[Test Example 4-1] Preparation of Cell-Free Filtrate

The cell-free filtrates of *Lactobacillus sakei* MD_honeysuckle obtained in Example 2 were prepared.
The cell-free filtrates of the reference strain were also prepared by the same method.

[Test Example 4-2] Measurement of Total Polyphenol Content

Total polyphenol content was measured indirectly from the polyphenol content of gallic acid at a specific concentration.

Figure 7:
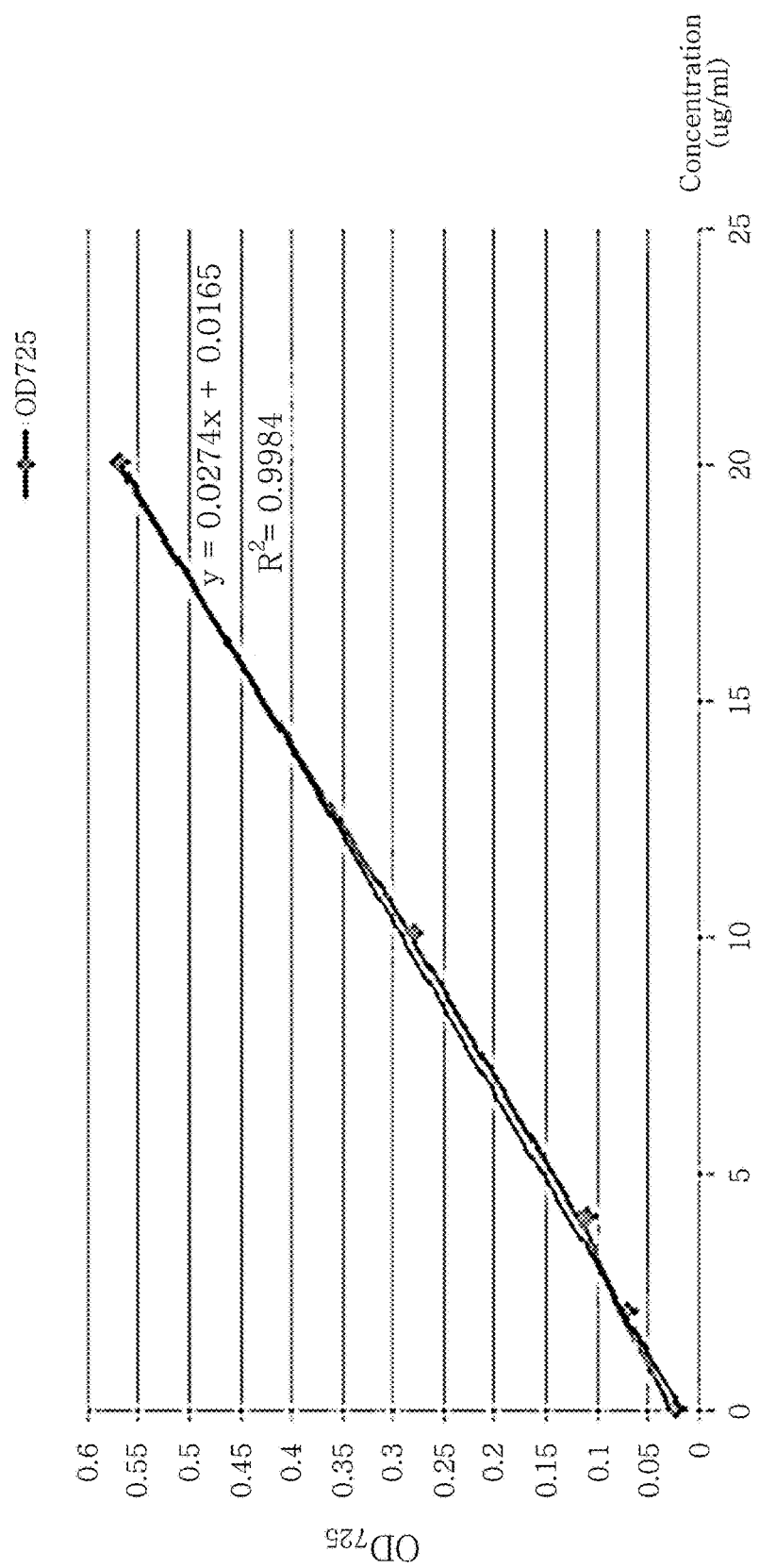
FIG. 7 shows a calibration curve using gallic acid for measuring total polyphenol content.
Figure 8:
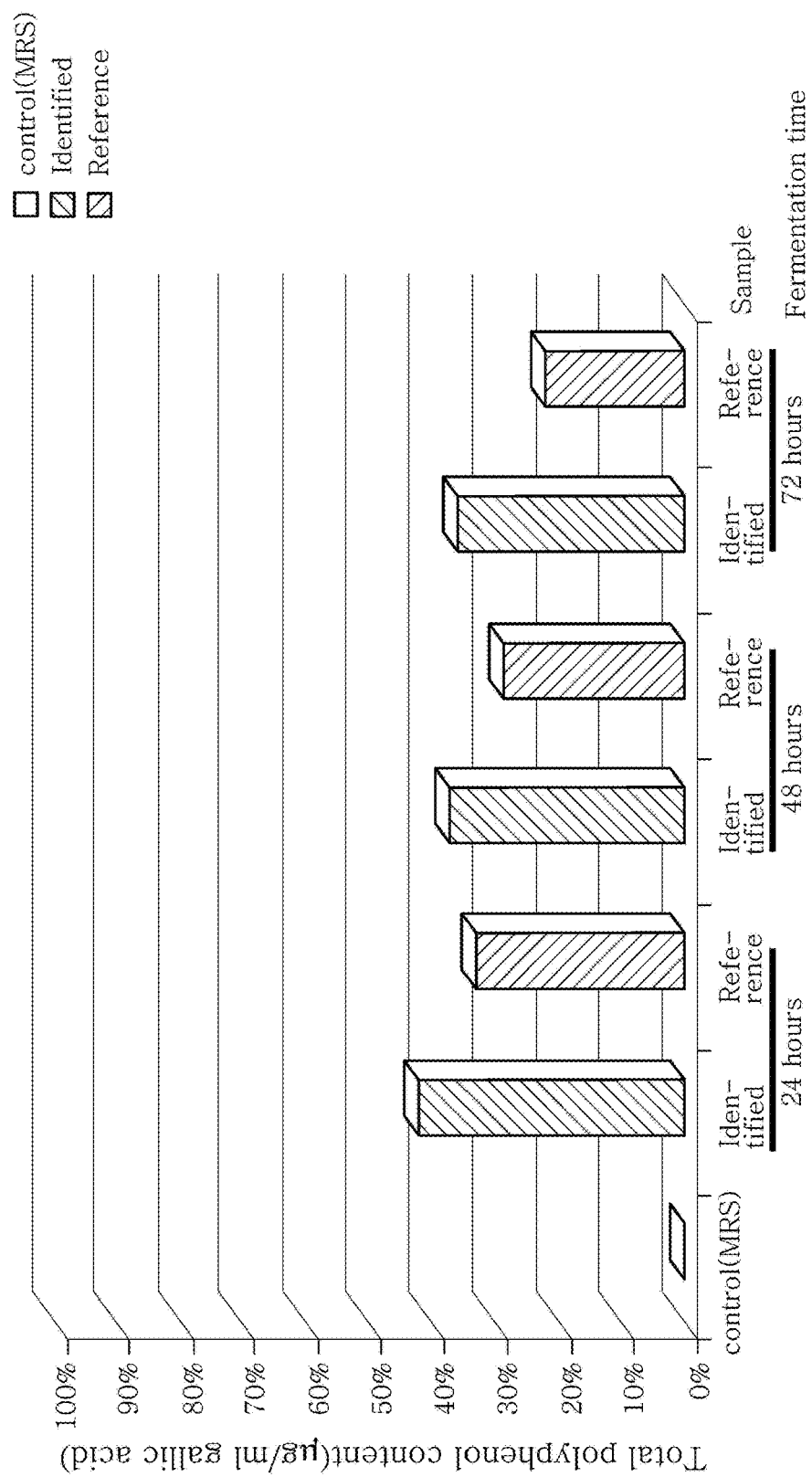
FIG. 8 shows the total polyphenol content of the identified strain and the reference strain.

1 mL of 0.2 M Folin-Ciocalteu's phenol reagent (Sigma Aldrich) was mixed with 1 mL of the cell-free filtrate of 1/10 diluted identified strain or reference strain and reacted at room temperature (25° C.) for 5 minutes. After adding 1 mL of 6% sodium bicarbonate (Sigma Aldrich) to the reaction solution, reaction was conducted at room temperature for 90 minutes. Then, absorbance was measured at 725 nm using a spectrophotometer (Biochrom Libra S22). Then, a calibration curve was constructed using 0 μg/mL, 2 μg/mL, 4 μg/mL, 10 μg/mL and 20 μg/mL gallic acid (Sigma Aldrich). The total polyphenol content of the sample was calculated in mg gallic acid/mL unit. The result is shown in FIG. 7. In the calibration curve y=0.0274x+0.0165 of FIG. 7, y denotes absorbance and x denotes the polyphenol content at the gallic acid concentration corresponding to the sample. The total polyphenol contents of the fermented products of the identified strain and the reference strain were calculated based on the calibration curve. The result is shown in FIG. 8.

[Test Example 5] Investigation of Melanogenesis Inhibiting Ability (B16 Melanoma Cell Melanin Assay)

Skin-whitening effect was evaluated as described below. B16 melanoma cells were seeded onto a 12-well plate at a density of $1.5 \times 10^5$ cells per well. DMEM (Dulbeco's modified Eagle's medium) supplemented with 10% fetal bovine serum was used and the cells were cultured for 24 hours (10% $CO_2$, 37° C.).

The 12-well plate onto which the B16 melanoma cells were seeded was treated with 200 nM melanocyte-stimulating hormone (MSH) and then the 12-well plate was treated with each sample (25, 50, 100 and 200 ppm). The test groups were: a group treated with sonicated identified strain (LBS sonication), a group treated with heat-killed identified strain (LBS heat), and a group treated with cultural filtrate of the identified strain (culture). As positive control groups, the cells were treated with kojic acid or arbutin at 100 ppm and then cultured for 3 days. The cells treated with nothing were used as a negative control group and those treated only with MSH was used as a vehicle group. After the treatment, the cell culture (extracellular melanin) was transferred to a 96-well plate and absorbance was measured at 475 nm. Based on the measurement result, melanin content was calculated from a standard curve constructed for synthetic melanin. The calculated melanin content was normalized to the total protein content for each group and the melanogenesis inhibiting ability was evaluated by comparing with the control groups. The experiment was repeated 3 times.

Figure 9:
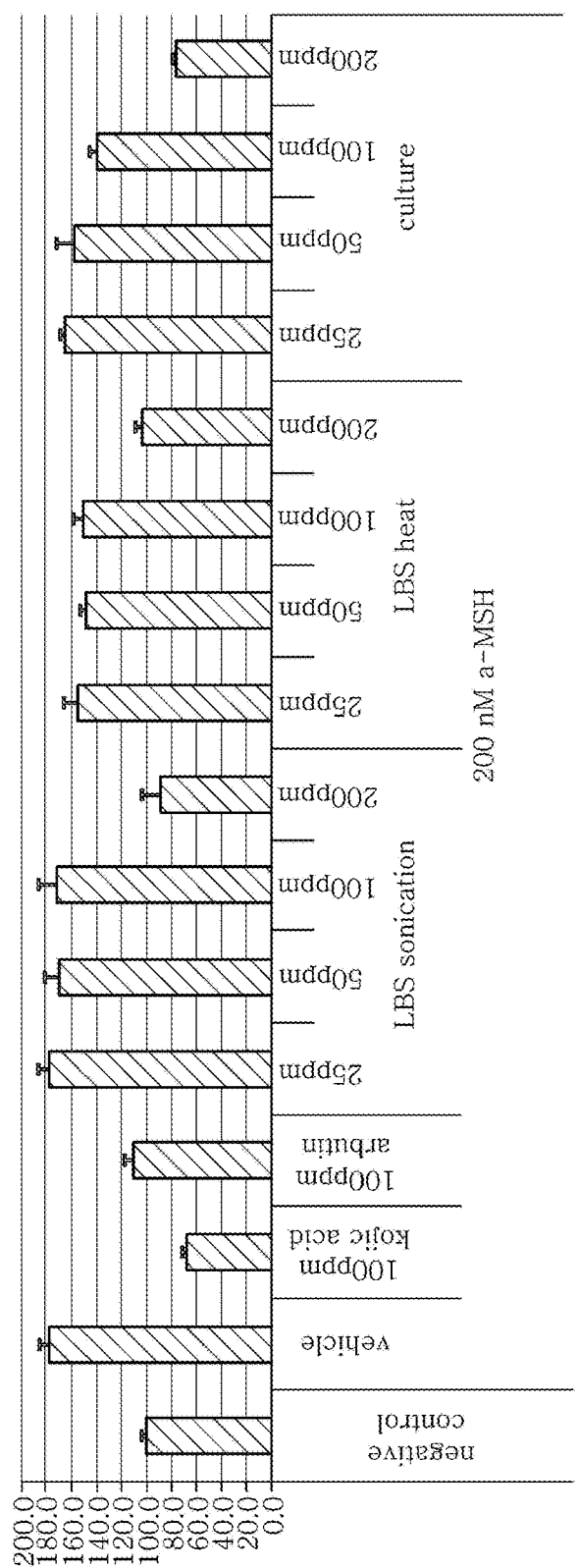
FIG. 9 shows the content of extracellular melanin after treatment with different samples relative to a negative control group (vehicle: treated only with MSH (melanocyte-stimulating hormone), kojic acid: treated with kojic acid, arbutin: treated with arbutin, the LBS sonication: treated with sonicated identified strain, LBS heat: treated with heat-killed identified strain, culture: treated with cultural filtrate of the identified strain).

The result is shown in Table 3 and the measured average value is shown in FIG. 9.

TABLE 3

| | | | extracellular OD475 | | | extracellular melanin, ppm | | | OD562 | | | protein contents, mg/ml | |
|---|---|---|---|---|---|---|---|---|---|---|---|---|---|
| | | | 1 | 2 | 3 | 1 | 2 | 3 | 1 | 2 | 3 | 1 | 2 |
| negative control | | | 0.212 | 0.206 | 0.222 | 104.00 | 101.00 | 109.00 | 1.035 | 1.0209 | 1.01543 | 0.577 | 0.569 |
| 200 nM a-MSH | vehicle | | 0.391 | 0.418 | 0.386 | 193.50 | 207.00 | 191.00 | 1.083 | 1.08437 | 1.08328 | 0.604 | 0.604 |
| | 100 ppm kojic acid | | 0.14 | 0.144 | 0.163 | 68.00 | 70.00 | 79.50 | 1.021 | 1.049 | 1.08768 | 0.569 | 0.585 |
| | 100 ppm arbutin | | 0.281 | 0.252 | 0.274 | 138.50 | 124.00 | 135.00 | 1.161 | 1.145 | 1.19709 | 0.646 | 0.638 |
| | LBS sonication | 25 ppm | 0.405 | 0.387 | 0.404 | 200.50 | 191.50 | 200.00 | 1.045 | 1.107 | 1.111 | 0.583 | 0.617 |
| | | 50 ppm | 0.381 | 0.382 | 0.396 | 188.50 | 189.00 | 196.00 | 1.178 | 1.047 | 1.095 | 0.656 | 0.584 |
| | | 100 ppm | 0.376 | 0.38 | 0.366 | 188.00 | 168.00 | 181.00 | 1.163 | 1.042 | 0.963 | 0.648 | 0.581 |
| | | 200 ppm | 0.194 | 0.174 | 0.21 | 95.00 | 85.00 | 103.00 | 1.111 | 1.047 | 0.951 | 0.619 | 0.584 |
| | LBS heat | 25 ppm | 0.332 | 0.33 | 0.373 | 164.00 | 163.00 | 184.50 | 1.092 | 1.061 | 1.077 | 0.608 | 0.591 |
| | | 50 ppm | 0.326 | 0.332 | 0.317 | 161.00 | 164.00 | 156.50 | 1.074 | 1.041 | 1.065 | 0.599 | 0.580 |
| | | 100 ppm | 0.307 | 0.334 | 0.348 | 151.50 | 165.00 | 172.00 | 1.042 | 1.051 | 1.08 | 0.581 | 0.586 |
| | | 200 ppm | 0.228 | 0.225 | 0.252 | 112.00 | 110.50 | 124.00 | 1.102 | 1.072 | 1.101 | 0.614 | 0.597 |
| | Culture | 25 ppm | 0.374 | 0.347 | 0.359 | 185.00 | 171.50 | 182.50 | 1.078 | 1.045 | 1.077 | 0.601 | 0.583 |
| | | 50 ppm | 0.387 | 0.329 | 0.341 | 191.50 | 162.50 | 168.50 | 1.08 | 1.055 | 1.09 | 0.602 | 0.588 |
| | | 100 ppm | 0.296 | 0.324 | 0.313 | 146.00 | 160.00 | 154.50 | 1.063 | 1.107 | 1.05 | 0.593 | 0.617 |
| | | 200 ppm | 0.171 | 0.173 | 0.173 | 83.50 | 84.50 | 84.50 | 1.05 | 1.108 | 1.076 | 0.585 | 0.617 |

| | | protein contents, mg/ml | melanin/protein, ug/mg | | | extracellular melanin, % of control | | | | |
|---|---|---|---|---|---|---|---|---|---|---|
| | | 3 | 1 | 2 | 3 | 1 | 2 | 3 | | |
| negative control | | 0.566 | 180.2 | 177.4 | 192.5 | 98.3 | 96.7 | 105.0 | 100.0 | 4.4 |
| 200 nM a-MSH | vehicle | 0.604 | 320.6 | 342.6 | 316.4 | 174.9 | 186.8 | 172.6 | 178.1 | 7.7 |
| | 100 ppm kojic acid | 0.605 | 119.4 | 119.7 | 131.2 | 65.1 | 65.3 | 71.5 | 67.3 | 3.7 |
| | 100 ppm arbutin | 0.666 | 214.2 | 194.5 | 202.6 | 116.8 | 106.1 | 110.5 | 111.1 | 5.4 |

TABLE 3-continued

| | | | | | | | | | | |
|---|---|---|---|---|---|---|---|---|---|---|
| LBS sonication | 25 ppm | 0.619 | 344.1 | 310.5 | 323.1 | 187.7 | 169.3 | 176.2 | 177.8 | 9.3 |
| | 50 ppm | 0.610 | 287.4 | 323.8 | 321.2 | 156.7 | 176.6 | 175.2 | 169.5 | 11.1 |
| | 100 ppm | 0.537 | 287.2 | 323.6 | 336.8 | 156.6 | 176.5 | 183.7 | 172.3 | 14.0 |
| | 200 ppm | 0.531 | 153.5 | 145.6 | 194.0 | 83.7 | 79.4 | 105.8 | 89.6 | 14.2 |
| LBS heat | 25 ppm | 0.600 | 269.5 | 275.6 | 307.4 | 147.0 | 150.3 | 167.6 | 155.0 | 11.1 |
| | 50 ppm | 0.594 | 269.0 | 282.6 | 263.6 | 146.7 | 154.1 | 143.8 | 148.2 | 5.3 |
| | 100 ppm | 0.602 | 260.8 | 281.6 | 285.8 | 142.2 | 153.6 | 155.9 | 150.6 | 7.3 |
| | 200 ppm | 0.613 | 182.4 | 184.9 | 202.1 | 99.5 | 100.9 | 110.2 | 103.5 | 5.9 |
| Culture | 25 ppm | 0.600 | 307.9 | 294.4 | 304.1 | 167.9 | 160.5 | 165.8 | 164.7 | 3.8 |
| | 50 ppm | 0.607 | 318.2 | 276.3 | 277.4 | 173.5 | 150.7 | 151.3 | 158.5 | 13.0 |
| | 100 ppm | 0.585 | 246.4 | 259.4 | 263.9 | 134.4 | 141.5 | 143.9 | 139.9 | 5.0 |
| | 200 ppm | 0.600 | 142.6 | 136.9 | 140.9 | 77.8 | 74.6 | 76.8 | 76.4 | 1.6 |

What is claimed is:

1. A method for improving a skin condition of a subject, which comprises administering an effective amount of a cultured cell-free filtrate of *Lactobacillus sakei* MD_honeysuckle to a subject in need thereof, wherein accession number of *Lactobacillus sakei* MD_honeysuckle is KCTC 12675BP.

2. The method according to claim 1, wherein the improving of the skin condition is for improving aging of the subject.

3. The method according to claim 1, wherein the improving of the skin condition is for whitening the skin of the subject.

4. The method according to claim 1, wherein the improving of the skin condition is for improving skin wrinkles of the subject.

5. The method according to claim 1, wherein the *Lactobacillus sakei* MD_honeysuckle is isolated from *Lonicera japonica* Thunb.

6. The method according to claim 1, wherein the *Lactobacillus sakei* MD_honeysuckle comprises a 16S rRNA of SEQ ID NO 1.

7. The method according to claim 1, wherein the cultured cell-free filtrate of *Lactobacillus sakei* MD_honeysuckle is administered in the form of a composition and the composition is a cosmetic, pharmaceutical or health food composition.

8. The method according to claim 3, wherein the cultured cell-free filtrate of *Lactobacillus sakei* MD_honeysuckle inhibits the production of melanocytes.

* * * * *